(12) United States Patent
Butani et al.

(10) Patent No.: US 11,020,066 B2
(45) Date of Patent: Jun. 1, 2021

(54) SYSTEM AND METHOD FOR CABINET X-RAY SYSTEMS WITH STATIONARY X-RAY SOURCE ARRAY

(71) Applicant: KUB TECHNOLOGIES, INC., Stratford, CT (US)

(72) Inventors: Vikram Butani, Stratford, CT (US); Yan Chen, Stratford, CT (US); Chester Lowe, Stratford, CT (US); Vignesh Mandalapa-Bhoopathy, Stratford, CT (US); Edwin Maria-Selvaraj, Stratford, CT (US); Roberto Velasco, Stratford, CT (US); Peter Yasutake, Stratford, CT (US)

(73) Assignee: Kub Technologies, Inc., Stratford, CT (US)

( * ) Notice: Subject to any disclaimer, the term of this patent is extended or adjusted under 35 U.S.C. 154(b) by 0 days.

(21) Appl. No.: 16/708,963

(22) Filed: Dec. 10, 2019

(65) Prior Publication Data

US 2020/0182807 A1 Jun. 11, 2020

Related U.S. Application Data

(60) Provisional application No. 62/777,389, filed on Dec. 10, 2018.

(51) Int. Cl.
*A61B 6/03* (2006.01)
*G01N 23/044* (2018.01)
(Continued)

(52) U.S. Cl.
CPC ............... *A61B 6/025* (2013.01); *A61B 6/40* (2013.01); *A61B 6/4007* (2013.01); *A61B 6/42* (2013.01);
(Continued)

(58) Field of Classification Search
CPC ......... A61B 6/025; A61B 6/40; A61B 6/4007; A61B 6/42; A61B 6/4208; A61B 6/4258;
(Continued)

(56) References Cited

U.S. PATENT DOCUMENTS 5,872,828 A * 2/1999 Niklason ................ A61B 6/025
378/23
6,028,910 A * 2/2000 Kirchner .............. G01N 23/046
378/22

(Continued)

*Primary Examiner* — Allen C. Ho
(74) *Attorney, Agent, or Firm* — Ziegler IP Law Group, LLC

(57) ABSTRACT

The present disclosure relates to the field of a cabinet x-ray incorporating a stationary x-ray source array, and an x-ray detector, for the production of organic and non-organic images. Stationary x-ray digital cabinet tomosynthesis systems and related methods are disclosed. According to one aspect, the subject matter described herein can include an x-ray tomosynthesis system having a plurality of stationary field emission x-ray sources configured to irradiate a location for positioning an object to be imaged with x-ray beams to generate projection images of the object. An x-ray detector can be configured to detect the projection images of the object. A projection image reconstruction function can be configured to reconstruct tomography images of the object based on the projection images of the object. In the preferred embodiment, the x-ray source or sources are statically affixed in a range from about 350° to and including about 10°.

20 Claims, 11 Drawing Sheets

(51) Int. Cl.
| | |
|---|---|
| *A61B 6/02* | (2006.01) |
| *G01N 23/083* | (2018.01) |
| *G01N 23/20025* | (2018.01) |
| *A61B 6/00* | (2006.01) |
| *G01N 23/04* | (2018.01) |

(52) U.S. Cl.
CPC .......... *A61B 6/4208* (2013.01); *A61B 6/4258* (2013.01); *A61B 6/44* (2013.01); *A61B 6/4405* (2013.01); *A61B 6/4411* (2013.01); *A61B 6/4429* (2013.01); *A61B 6/502* (2013.01); *A61B 6/508* (2013.01); *A61B 6/54* (2013.01); *A61B 6/542* (2013.01); *A61B 6/58* (2013.01); *A61B 6/588* (2013.01); *A61B 6/589* (2013.01); *G01N 23/04* (2013.01); *G01N 23/044* (2018.02); *G01N 23/083* (2013.01); *G01N 23/20025* (2013.01); *G01N 2223/318* (2013.01); *G01N 2223/6123* (2013.01); *G01N 2223/6126* (2013.01)

(58) Field of Classification Search
CPC ....... A61B 6/44; A61B 6/4405; A61B 6/4411; A61B 6/4429; A61B 6/4435; A61B 6/502; A61B 6/58; A61B 6/588; A61B 6/589; A61B 6/508; G01N 23/04; G01N 23/044
USPC .......... 378/9, 10, 21, 22, 25, 26, 37, 62, 92, 378/189, 196–198, 207, 208
See application file for complete search history.

(56) References Cited

U.S. PATENT DOCUMENTS

| | | | | |
|---|---|---|---|---|
| 6,236,708 B1* | 5/2001 | Lin | ........................ | A61B 6/025 378/22 |
| 6,628,745 B1* | 9/2003 | Annis | .................... | A61B 6/032 378/10 |
| 6,707,878 B2* | 3/2004 | Claus | .................... | G06T 11/005 378/210 |
| 6,882,700 B2* | 4/2005 | Wang | ..................... | A61B 6/025 378/197 |
| 6,940,943 B2* | 9/2005 | Claus | .................... | G01N 23/044 378/27 |
| 6,970,531 B2* | 11/2005 | Eberhard | ............... | A61B 6/025 378/197 |
| 6,973,160 B2* | 12/2005 | Matsumoto | .............. | A61B 6/02 348/E5.086 |
| 6,993,111 B1* | 1/2006 | Annis | .................. | G01N 23/044 378/57 |
| 7,023,950 B1* | 4/2006 | Annis | ....................... | H01J 35/30 378/2 |
| 7,110,490 B2* | 9/2006 | Eberhard | ............. | A61B 6/4028 378/23 |
| 7,123,683 B2* | 10/2006 | Tsujii | ................... | A61B 6/0457 378/26 |
| 7,177,390 B2* | 2/2007 | Martin | ................. | A61B 6/4405 378/25 |
| 7,330,529 B2* | 2/2008 | Kautzer | ................. | A61B 6/025 378/25 |
| 7,356,113 B2* | 4/2008 | Wu | ....................... | G06T 11/006 378/27 |
| 7,453,979 B2* | 11/2008 | Sendai | ................... | A61B 6/025 378/23 |
| 7,463,713 B2* | 12/2008 | Mertelmeier | .......... | A61B 6/025 378/22 |
| 7,515,682 B2* | 4/2009 | Li | ......................... | A61B 6/025 378/210 |
| 7,558,366 B2* | 7/2009 | Barth | .................... | G06T 11/006 378/197 |
| 7,567,647 B1* | 7/2009 | Maltz | .................... | A61B 6/025 378/21 |
| 7,697,661 B2* | 4/2010 | Souchay | ................ | A61B 6/025 378/21 |
| 7,708,462 B2* | 5/2010 | Fujiwara | ................ | A61B 6/025 378/206 |
| 7,751,528 B2* | 7/2010 | Zhou | ...................... | A61B 6/025 378/21 |
| 7,778,388 B2* | 8/2010 | Sendai | ................... | A61B 6/025 378/22 |
| 7,831,296 B2* | 11/2010 | DeFreitas | .............. | A61B 6/025 600/427 |
| 7,885,378 B2* | 2/2011 | Kopans | ................. | A61B 6/025 378/13 |
| 7,945,014 B2* | 5/2011 | Mertelmeier | .......... | A61B 6/025 378/21 |
| 7,945,015 B2* | 5/2011 | Tsujii | ....................... | A61B 6/00 378/124 |
| 7,965,812 B2* | 6/2011 | Hanke | ................... | A61B 6/502 378/21 |
| 8,031,834 B2* | 10/2011 | Ludwig | ................. | A61B 6/025 378/22 |
| 8,094,773 B2* | 1/2012 | Boese | .................... | A61B 6/025 378/21 |
| 8,149,987 B2* | 4/2012 | Ogura | ................... | A61B 6/025 378/115 |
| 8,184,765 B2* | 5/2012 | Akahori | ................. | A61B 6/032 378/25 |
| 8,284,894 B2* | 10/2012 | Poorter | ................. | A61B 6/025 378/21 |
| 8,363,050 B2* | 1/2013 | Ludwig | ................. | A61B 6/025 345/419 |
| 8,559,593 B2* | 10/2013 | Akahori | ................ | A61B 6/032 378/115 |
| 8,571,174 B2* | 10/2013 | Smith | .................... | A61B 6/025 378/37 |
| 8,576,988 B2* | 11/2013 | Lewalter | .............. | A61B 6/4028 378/126 |
| 8,605,854 B2* | 12/2013 | Hoernig | ................. | A61B 6/502 378/37 |
| 8,619,946 B2* | 12/2013 | Hanke | ................... | H01J 35/10 378/124 |
| 8,699,657 B2* | 4/2014 | Baeumer | ............... | A61B 6/032 250/494.1 |
| 8,699,661 B2* | 4/2014 | Jang | ...................... | A61B 6/4007 378/37 |
| 8,817,947 B2* | 8/2014 | Vedantham | ........... | A61B 6/022 378/21 |
| 8,848,864 B2* | 9/2014 | Jeong | ................... | G01N 23/046 378/25 |
| 9,138,193 B2 | 9/2015 | Lowe et al. | | |
| 9,146,199 B2* | 9/2015 | Jang | ...................... | G01N 23/044 |
| 9,316,746 B2* | 4/2016 | Nishino | ................... | G01T 1/17 |
| 9,364,190 B2* | 6/2016 | Lee | ...................... | A61B 6/588 |
| 9,408,577 B2* | 8/2016 | Tamura | ................. | A61B 6/025 |
| 9,412,552 B2* | 8/2016 | Aoki | ..................... | H01J 35/065 |
| 9,414,800 B2* | 8/2016 | Takagi | ................. | A61B 6/5241 |
| 9,439,614 B2* | 9/2016 | Jang | ...................... | A61B 6/03 |
| 9,517,043 B2* | 12/2016 | Tamura | ................. | A61B 6/025 |
| 9,642,581 B2 | 5/2017 | Lowe et al. | | |
| 9,730,669 B2* | 8/2017 | Lee | ........................ | A61B 6/545 |
| 9,993,214 B2* | 6/2018 | Fukuyo | .................. | G06T 11/60 |
| 10,488,351 B2* | 11/2019 | Butani | ................. | G01N 23/044 |
| 10,575,812 B2* | 3/2020 | Kobayashi | .............. | A61B 6/00 |
| 10,631,810 B2* | 4/2020 | Arai | ...................... | A61B 6/025 |
| 10,646,178 B2* | 5/2020 | Butani | ................. | A61B 8/4416 |
| 10,652,990 B2* | 5/2020 | Butani | ................. | A61B 6/467 |
| 10,670,545 B2* | 6/2020 | Butani | ................. | A61B 6/4435 |
| 10,672,517 B2* | 6/2020 | Weidner | ................ | G16H 30/20 |
| 10,729,399 B2* | 8/2020 | Butani | ................. | A61B 6/025 |
| 10,772,576 B2* | 9/2020 | Han | ..................... | A61B 6/4464 |
| 10,779,784 B2* | 9/2020 | Fukuda | ................. | G16H 50/30 |
| 10,806,420 B2* | 10/2020 | Mohammadi | ......... | H01J 35/066 |
| 10,810,766 B2* | 10/2020 | Fukuda | ................. | A61B 6/025 |
| 10,830,712 B2* | 11/2020 | Butani | ................. | A61B 6/502 |
| 10,837,921 B2* | 11/2020 | Butani | ................. | G01N 23/046 |
| 2018/0067061 A1 | 3/2018 | Butani et al. | | |

\* cited by examiner

FRONT VIEW INTO CABINET
Door Open

**Typical Example of an X-ray Cabinet System

View in Sample Chamber with Door Open with
X-ray source at position (14) Top Center Lateral View of X-Ray Source
Mounted to Swing Arm at position (14)

Basic Rotation with Sample on Tray
to affect Geometric Magnification

SYSTEM AND METHOD FOR CABINET X-RAY SYSTEMS WITH STATIONARY X-RAY SOURCE ARRAY

CROSS-REFERENCE TO RELATED APPLICATIONS

This application claims priority to and the benefit of U.S. Provisional Patent Application Ser. No. 62/777,389 filed Dec. 10, 2018, the disclosure of which is incorporated herein by reference in its entirety.

BACKGROUND

Field

The present disclosure relates to the field of a cabinet x-ray incorporating a system and method for utilizing fixed/stationary x-ray source array to attain the multiple projections necessary for specimen tomosynthesis more appropriately aspects of the disclosed embodiments are directed to the field of cabinet x-ray imaging of excised human tissue, and more specifically, to a system and method for obtaining and processing cabinet x-ray image data for tomosynthesis reconstruction allowing for a three-dimensional image of the specimen with the capability of attaining images of the specimen with geometric magnification and the purpose of such devices.

Background

Imaging of a patient's tissue has become a common screening tool and/or diagnostic aid in modern medicine. Breast cancer remains an important threat to women's health and is the most common cancer among women today. One strategy for dealing with breast cancer is early detection of the cancer so that it may be treated prior to the cancer metastasizing throughout the body. This causes an increase in the number of surgical procedures performed involving excision of cancerous tissue or calcifications, such as ductal carcinoma in situ (DCIS).

The excision of Ductal carcinoma in situ (DCIS) is a challenging task. In order to assure that the complete DCIS lump including a cancer-free margin has been excised, the following steps may be undertaken. A pre-operational planning based on mammograms is performed carefully in order to assess the size and the location of the lump. The location of the lump is marked utilizing guide wires/markers. During the lumpectomy, the excised tissue is examined using x-ray imaging in order to assess whether its margin is cancer-free. If it is found that the excised specimen has an insufficient margin of cancer-free tissue, the surgeon removes more tissue.

Currently, x-ray images obtained are only available in two-dimensional mode and as such orthogonal views of the sample must be obtained by physically rotating the specimen to verify the margins. The breast surgeon relies on the radiogram to verify removal of the complete lump. If necessary, the breast surgeon may have to identify additional breast tissue that must be excised to ensure a clear margin. This can be an error prone and time consuming task that is performed under significant time pressure whilst the anesthetized patient is still lying on the operating table.

In typical x-ray imaging, a patient's breast sample is immobilized and contained in a specimen container. The sample is placed between an x-ray source and a digital imaging device (detector) to create a two-dimensional radiographic image of the sample. To ensure that margins are attained, at least 2 orthogonal images must be taken of the sample (90 degrees apart). The problem that arises with the above scenario is that the tissue, being somewhat fluid, may displace when it is imaged in either position, which may cause a false measurement to the breast surgeon. It would be advantageous to be able to image the sample from a greater number of different positions of the source and receptor relative to the sample while maintaining the sample stationary or in a fixed position.

Digital tomosynthesis combines digital image capture and processing with simple tube/detector motion as used in conventional radiographic tomography. Although there are some similarities to CT, it is a separate technique. In CT, the source/detector makes a complete 360-degree rotation about the subject obtaining a complete set of data from which images may be reconstructed. In digital tomosynthesis, a small change of flux created by only a small rotation angle with a small number of exposures are used. This set of data can be digitally processed to yield images similar to conventional tomography with a limited depth of field. However, because the image processing is digital, a series of slices at different depths and with different thicknesses can be reconstructed from the same acquisition, saving time.

Image data taken at the different imaging positions can be processed to generate tomosynthetic images of selected slices of the sample. The images can be of thin slices, essentially planar sections through the specimen, as in CT slices. Alternatively, they can be varying thickness.

The isocenter of the image acquisition geometry is located below the sample, on the surface of the detector. The phase shifts created as a result of this arrangement are compensated for, while processing the resultant dataset. The tomosynthetic images are then generated from the generated data set.

There may be cases where magnification of the specimen should be obtained to provide a better image or visualization of the anomalies present. Digital magnification can distort and/or pixelate an image at an "x" magnification whereas a geometric magnification would provide a magnification of an "x" power without any distortion of the sample.

It is believed that no cabinet specimen tomosynthesis systems utilizing geometric magnification are commercially available currently for clinical use in specimen imaging, and that improvements in x-ray imaging and tomosynthesis are a desired goal. Accordingly, it is believed that there is a need for improved and practical tomosynthesis of breast specimens with the capability of geometric magnification It would be advantageous to have a cabinet x-ray system for specimen imaging that could create, via digital tomosynthesis, a three-dimensional image for the breast surgeon to ensure that a proper margin around the diseased tissue has been excised in an expedient manner.

To address this, in one aspect of the present disclosure include a sample tray holding the specimen may be elevated in the sample chamber above the detector to allow for a geometric magnification of the specimen imaged and to create images which would compensate and/or delete digital distortion.

Specimen radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

Imaging of a patient's tissue has become a common screening tool and/or diagnostic aid in modern medicine. Breast cancer remains an important threat to women's health and is the most common cancer among women today. One strategy for dealing with breast cancer is early detection of the cancer so that it may be treated prior to the cancer metastasizing throughout the body. This causes an increase in the number of surgical procedures performed involving excision of cancerous tissue or calcifications, such as ductal carcinoma in situ (DCIS).

The excision of DCIS is a challenging task. In order to assure that the complete DCIS lump including a cancer-free margin has been excised, the following steps may be undertaken. A pre-operational planning based on mammograms is performed carefully in order to assess the size and the location of the lump. The location of the lump is marked utilizing guide wires/markers. During the lumpectomy, the excised tissue is examined using x-ray imaging in order to assess whether its margin is cancer-free. If it is found that the excised specimen has an insufficient margin of cancer-free tissue, the surgeon removes more tissue.

Currently, x-ray images obtained are only available in two-dimensional mode and as such orthogonal views of the sample must be obtained by physically rotating the specimen to verify the margins. The breast surgeon relies on the radiogram to verify removal of the complete lump. If necessary, the breast surgeon may have to identify additional breast tissue that must be excised to ensure a clear margin. This is an error prone and time consuming task that is performed under significant time pressure whilst the anesthetized patient is still lying on the operating table.

In typical x-ray imaging, a patient's breast sample is immobilized and contained in a specimen container. The sample is placed between an x-ray source and a digital imaging device (detector) to create a two-dimensional radiographic image of the sample. To ensure that margins are attained, at least 2 orthogonal images must be taken of the sample (90 degrees apart). The problem that arises with the above scenario is that the tissue, being somewhat fluid, may displace when it is imaged in either position, which may cause a false measurement to the breast surgeon. It would be advantageous to be able to image the sample from a greater number of different positions of the source and receptor relative to the sample while maintaining the sample stationary or in a fixed position.

Digital tomosynthesis combines digital image capture and processing with simple tube/detector motion as used in conventional radiographic tomography. Although there are some similarities to CT, it is a separate technique. In CT, the source/detector makes a complete 360-degree rotation about the subject obtaining a complete set of data from which images may be reconstructed. In digital tomosynthesis, a small change of flux created by only a small rotation angle with a small number of exposures are used. This set of data can be digitally processed to yield images similar to conventional tomography with a limited depth of field. However, because the image processing is digital, a series of slices at different depths and with different thicknesses can be reconstructed from the same acquisition, saving time.

Image data taken at the different imaging positions can be processed to generate tomosynthetic images of selected slices of the sample. The images can be of thin slices, essentially planar sections through the specimen, as in CT slices. Alternatively, they can be varying thickness.

The isocenter of the image acquisition geometry is located below the sample, on the surface of the detector. The phase shifts created as a result of this arrangement are compensated for, while processing the resultant dataset. The tomosynthetic images are then generated from the generated data set.

A cabinet specimen radiography x-ray tube is used to collect the projection images by moving 10-50 degrees around the object.

Two tube rotation modes have been developed. One commercially-available system uses a stop-and-shoot technique. The gantry makes a full stop before taking each projection image. Acceleration/deceleration can cause mechanical instability of the system. A continuous rotation mode is used in other commercially available systems. The gantry keeps a constant rotation speed during the whole imaging process. In this case, the x-ray focal spot size is enlarged along the motion direction. The value of the enlargement depends on the rotation speed and the exposure time. It has been reported that the x-ray focal spot moves about 1 mm in a typical scan. This does not leave room for further reduction of the total scanning time, which will require a faster gantry rotation and a larger focal spot blurring.

It would be beneficial to provide x-ray imaging systems and methods having reduced data collection times and improvements for resolution and speed of acquisition and computation. One or more such improvements can enable new applications for x-ray imaging of the breast specimen tissue as well as other objects. Accordingly, it is desirable to provide x-ray imaging systems and methods having one or more of these improvements.

It is believed that no cabinet specimen tomosynthesis systems utilizing a stationary or a multiple of stationary x-ray sources is commercially available currently for clinical use in specimen imaging, and that improvements in x-ray imaging and tomosynthesis are a desired goal. Accordingly, it is believed that there is a need for improved and practical tomosynthesis of breast specimens.

It would be advantageous to have a cabinet x-ray system for specimen imaging that could create, via digital tomosynthesis, a three-dimensional image for the breast surgeon to ensure that a proper margin around the diseased tissue has been excised in an expedient manner.

The disclosure as related above explains how embodiments of the present disclosure would relate to specimen radiography but the disclosure is not isolated to specimen radiography but may be utilized for non-destructive testing, pathology as well as any radiographic analysis, organic and non-organic, requiring a cabinet x-ray system utilizing an x-ray source or system within the confines of the cabinet x-ray system.

SUMMARY

The present disclosure relates to the field of a cabinet x-ray incorporating a stationary x-ray tube or array, and an x-ray detector, for the production of tomographic organic and non-organic images.

It is an object of the presently disclosed subject matter to provide novel stationary x-ray digital cabinet tomosynthesis systems and related methods.

An object of the presently disclosed subject matter having been stated hereinabove, and which is achieved in whole or in part by the presently disclosed subject matter, other objects will become evident as the description proceeds when taken in connection with the accompanying drawings described hereinbelow In one embodiment, a cabinet x-ray system for obtaining specimen x-ray images, projection x-ray images, and reconstructed tomosynthetic x-ray images of a specimen is provided. The system includes a cabinet defining an interior chamber; a display; an x-ray system and a controller. The x-ray system includes an x-ray detector; a plurality of x-ray sources, wherein one of the plurality of x-ray sources is positioned at a standard imaging angle of approximately 0° relative to the x-ray detector; and a specimen platform. The controller is configured to: separately energize each of the plurality of x-ray sources separately to emit x-rays through the specimen to the x-ray detector such that the isocenter of the emitted x-rays of each of the plurality of x-ray sources is located at a surface of the x-ray detector; control the x-ray detector to collect projection x-ray images of the specimen when each of the plurality of x-ray sources are separately energized, wherein one of the projection x-ray images is a two-dimensional x-ray image taken at standard imaging angle of approximately 0°; create a tomosynthetic x-ray image reconstructed from a collection of projection x-ray images; process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image and the one or more reconstructed tomosynthetic x-ray images.

In another embodiment, a cabinet x-ray system for obtaining specimen x-ray images, projection x-ray images, and reconstructed tomosynthetic x-ray images of a specimen is provided. The system includes a cabinet defining an interior chamber; a display; an x-ray system and a controller. The x-ray system includes a flat panel x-ray detector; a plurality of x-ray sources, wherein one of the plurality of x-ray sources is positioned at a standard imaging angle of approximately 0° relative to the x-ray detector; and a specimen platform including a magnification tray that is positioned at a distance above the flat panel digital x-ray detector to facilitate geometric magnification imaging of the specimen in the cabinet. The controller is configured to separately energize each of the plurality of x-ray sources separately to emit x-rays through the specimen to the x-ray detector such that the isocenter of the emitted x-rays of each of the plurality of x-ray sources is located at a surface of the x-ray detector; control the x-ray detector to collect projection x-ray images of the specimen when each of the plurality of x-ray sources are separately energized, wherein one of the projection x-ray images is a two-dimensional x-ray image taken at standard imaging angle of approximately 0°; create a tomosynthetic x-ray image reconstructed from a collection of projection x-ray images; process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image and the one or more reconstructed tomosynthetic x-ray images.

In another embodiment a method for obtaining and varying a superimposed image of an x-ray image and an optical image of a specimen in a cabinet x-ray and optical image system is provided. The cabinet x-ray and optical image system comprises a cabinet defining an interior chamber; a display; an x-ray system and a controller. The x-ray system includes an x-ray detector; a plurality of x-ray sources, wherein one of the plurality of x-ray sources is positioned at a standard imaging angle of approximately 0° relative to the x-ray detector; and a specimen platform. The controller is configured to separately energize each of the plurality of x-ray sources separately to emit x-rays through the specimen to the x-ray detector such that the isocenter of the emitted x-rays of each of the plurality of x-ray sources is located at a surface of the x-ray detector; control the x-ray detector to collect projection x-ray images of the specimen when each of the plurality of x-ray sources are separately energized, wherein one of the projection x-ray images is a two-dimensional x-ray image taken at standard imaging angle of approximately 0°; create a tomosynthetic x-ray image reconstructed from a collection of projection x-ray images; process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image and the one or more reconstructed tomosynthetic x-ray images. The method includes controlling the x-ray detector to collect projection x-ray images of the specimen when each of the plurality of x-ray sources are separately energized, wherein one of the projection x-ray images is a two-dimensional x-ray image taken at standard imaging angle of approximately 0°; creating a tomosynthetic x-ray image reconstructed from a collection of projection x-ray images; processing the collection of the projection x-ray images in the controller into one or more reconstructed tomosynthetic x-ray images representing a volume of the specimen and relating to one or more image planes that are selectively the same or different from that of the two-dimensional x-ray image; and selectively displaying the two-dimensional x-ray image and the one or more reconstructed tomosynthetic x-ray images.

BRIEF DESCRIPTION OF THE DRAWINGS

To further clarify the above and other advantages and features of the present disclosure, a more particular description will be rendered by reference to specific embodiments thereof that are illustrated in the appended drawings. It is appreciated that these drawings depict only typical embodiments of the present disclosure and are therefore not to be considered limiting of its scope. The aspects of the present disclosure will be described and explained with additional specificity and detail through the use of the accompanying drawings in which.

DETAILED DESCRIPTION

The systems and methods of the present disclosure address the needs of the art by providing tomosynthesis apparatus and techniques for imaging breast specimens that overcome the shortfall of the data received from two-dimensional imaging systems. The aspects of the present disclosure enable the use of tomosynthesis to efficiently provide accurate three-dimensional imaging of a specimen in which overlapping images having differing attenuation characteristics by applying a three-dimensional reconstruction algorithm all in an x-ray cabinet with the option of providing geometric magnification of the specimen.

As used herein, the term "computer," "computer system" or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine readable instructions, program or library of routines capable of executing on a computer or computer system including computer readable program code.

Specimen Tomography Tomosynthesis is a three-dimensional specimen imaging system. It involves acquiring images of a sample at multiple viewpoints, typically over an arc or linear path. The three-dimensional image is constructed by the reconstruction of the multiple image data set.

Figure 1:
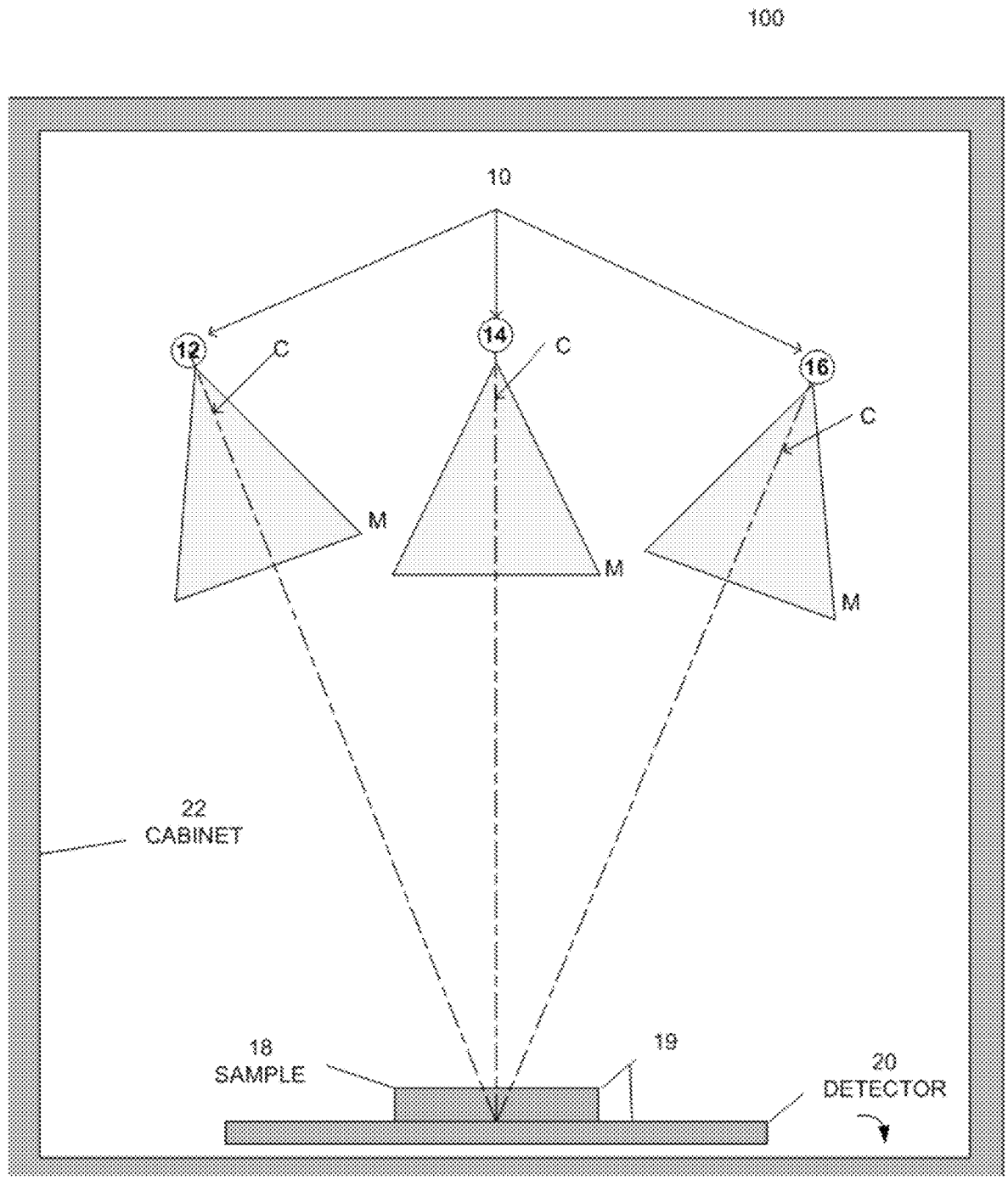
FIG. 1—Schematically illustrates one embodiment of the present disclosure including a front view of an X-ray source, a specimen/sample, and a digital detector, where the X-ray source moves relative to the specimen for imaging the specimen at different angles, in one embodiment of a system incorporating aspects of the present disclosure.

One embodiment of a system 100 incorporating aspects of the present disclosure is illustrated in FIG. 1. The system 100 is totally enclosed or housed in an X-ray cabinet 22. The aspects of the present disclosure include arc or linear travel of the x-ray source 10 over a 20° to 30° arc clockwise or counterclockwise between approximately 350° 12 to 0° 14 to 10° 16 or between approximately 340° 12 to 0° 14 to 20° 16 but may traverse an arc of up to 50°. The ranges recited herein are intended to be approximate and inclusive of start and endpoints. The detector 20 is stationary as is the sample 18 and is an x-ray detector and can include, for example, a flat panel x-ray detector, a flat panel digital x-ray detector, e.g. a CMOS x-ray detector. The reference "C" at each of the positions 12, 14, 16 of the X-ray source 10 in FIG. 1 refers to the point source of the X-ray beam. The reference "M" refers to the spread or fan of the X-ray beam.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the detector 20 may move or rotate, in accordance with one aspect of the present disclosure, the detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the detector 20 is stationary as is the sample 18. The sample 18 also referred to as the "object" or "imaging object" is disposed on or rests on the specimen platform 19 (which is a protective cover) or other surface of the detector 20.

The disclosures of U.S. Pat. Nos. 9,138,193 and 9,642,581 B2 Lowe, et. al., entitled "Specimen Radiography with Tomosynthesis in a Cabinet," and U.S. Pat. No. 10,488,351 B2 issued on 26 Nov. 2019, which corresponds to U.S. Patent Pub. No. 2018/0067061 entitled "Specimen Radiography with Tomosynthesis in a Cabinet with Geometric Magnification" are hereby incorporated by reference in their entirely into the present disclosure.

In operation, x-ray source 10 is energized to emit an x-ray beam throughout its travel. The x-ray beam travels through the sample 18 to the detector 16 and the multiple images collected at varying angles are stored and then utilized for the tomosynthesis reconstruction. With the sample 18, also referred to as the "object" or "imaging object", sitting on the detector 20 a 1:1 geometric magnification image is attained.

Different embodiments can utilize different ranges of motion of one or more of the x-ray source 10 and detector 20 as well as changing the angularity of one or both. The inventive aspects of the present disclosure differ from prior systems in that either both the detector 20 and x-ray source 10 move and/or the isocenter is above the sample 18 and not at the detector surface. In accordance with the aspects of the present disclosure, in one embodiment, the x-ray source 10 may be configured to move or rotate, as is described herein, while the detector 20 is configured to remain stationary or in a fixed position.

The detector 20 and associated electronics generate image data in digital form for each pixel at each of the angular positions 12, 14, 16 of X-ray source 10 and translations positions of the detector 20 relative to the sample 18. While only three positions 12, 14, 16 are illustrated in FIG. 1, in practice more images are taken at differing angles. For example, in one embodiment, images can be taken, i.e. at approximately every 1° of rotation or motion of the x-ray source 10.

In operation of one embodiment, X-ray source 10 is energized to emit an X-ray beam, generally throughout its travel along one or more of the paths or positions described above. The X-ray beam travels through the sample 18 to the detector 20 and the multiple images are collected by the detector 20 at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and detector 20 as well as changing the angularity of one or both. The inventive aspects of the present disclosure differ from the prior art in that in prior art systems either the detector 20 and X-ray source 10 and/or the isocenter is above the sample 18 and not at the detector surface. In accordance with the aspects of the present disclosure, in one embodiment, the X-ray source 10 is configured to move, as is described herein, while the detector 20 is configured to remain stationary or in a fixed position.

The detector 20 and associated electronics generate image data in digital form for each pixel at each of the angular positions 12, 14, 16 of X-ray source 10 and translation positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10.

Figure 2:
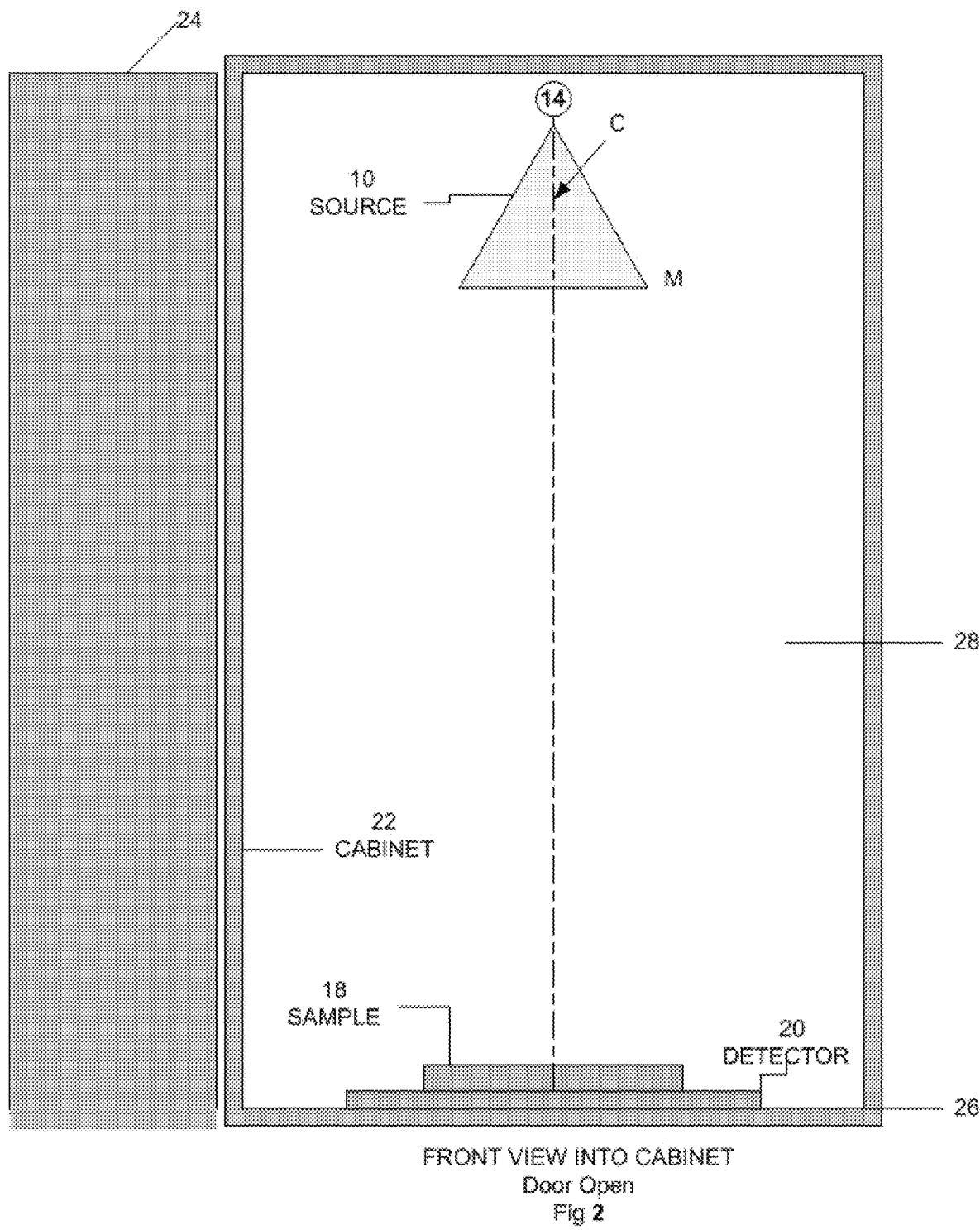
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
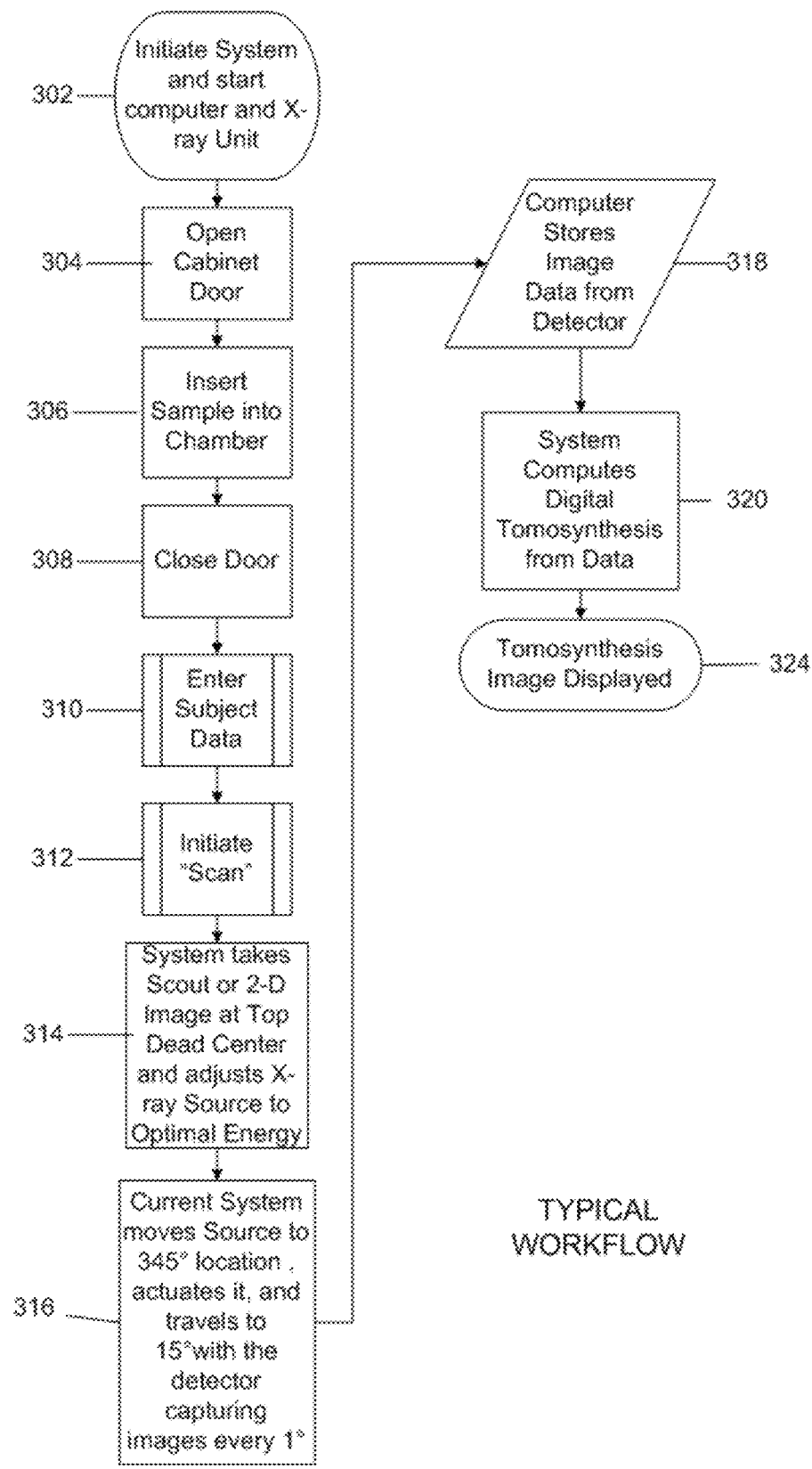
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system exemplified in FIG. 1, for example, is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2 and x-ray source 704 in FIGS. 7 and 7A discussed subsequently. The X-ray source 10 can then be moved to other positions, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Figure 4:
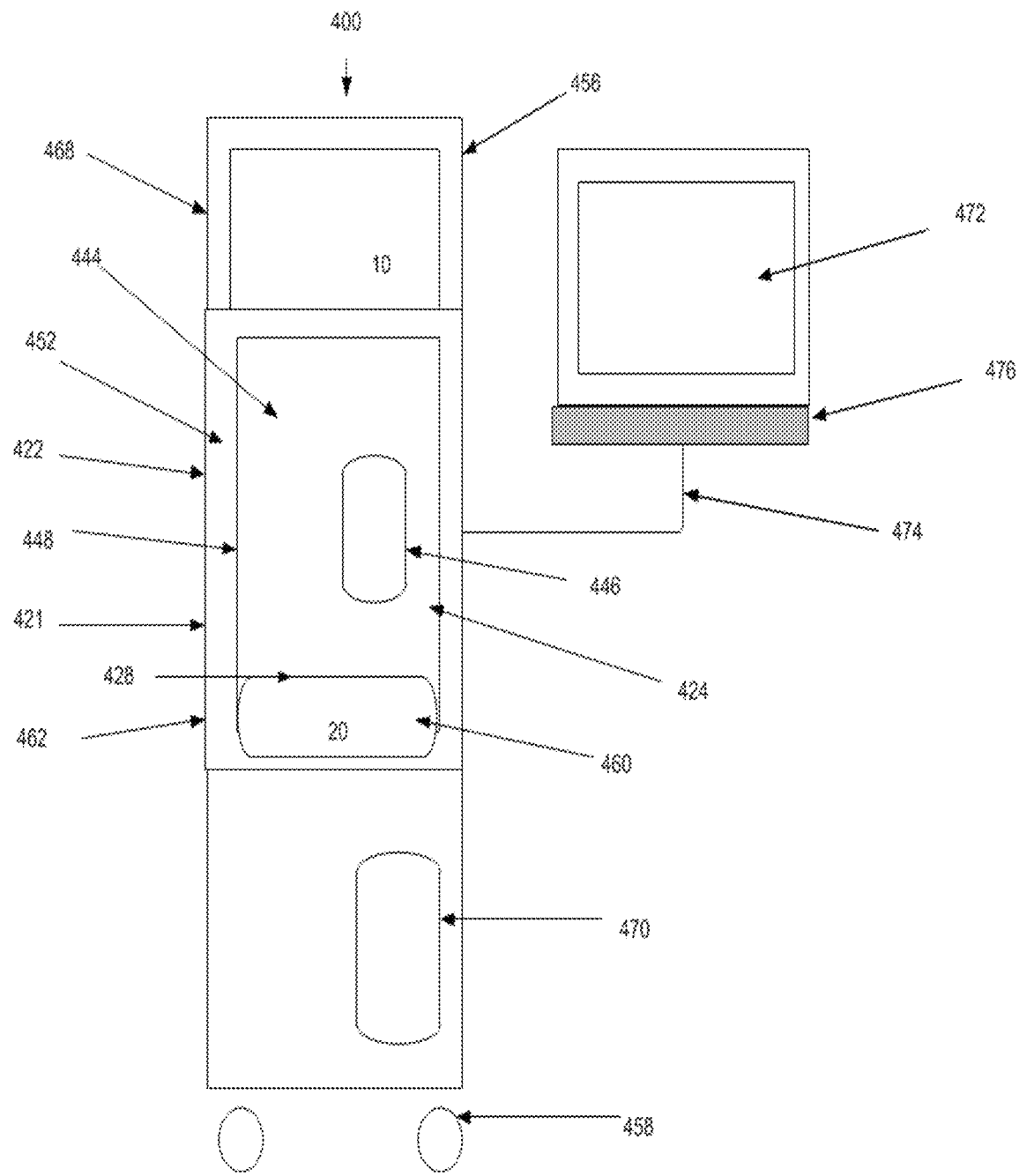
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
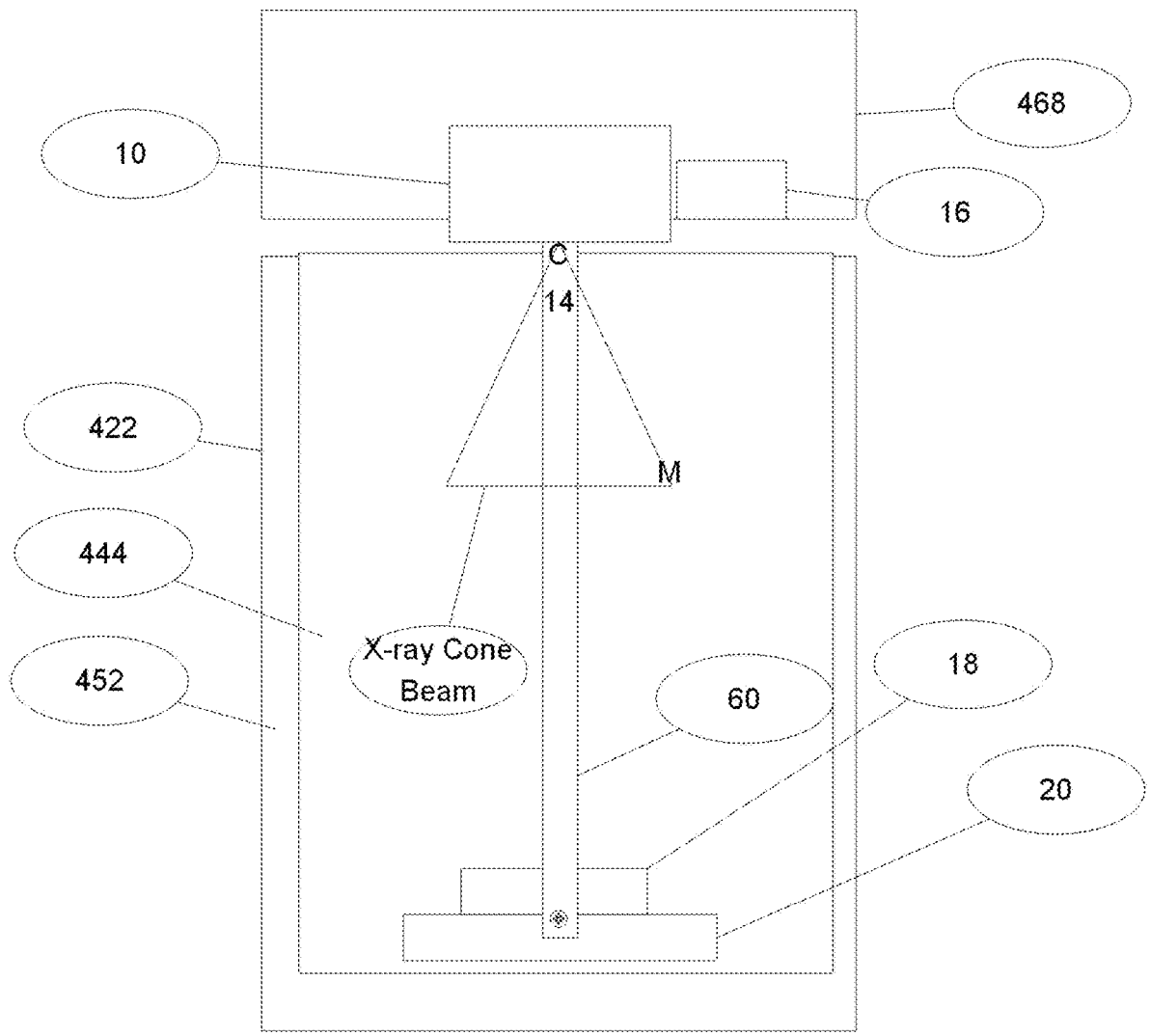
FIG. 5—Displays the sample chamber of the embodiment of FIG. 4 with the swing arm and a detector.
Figure 6:
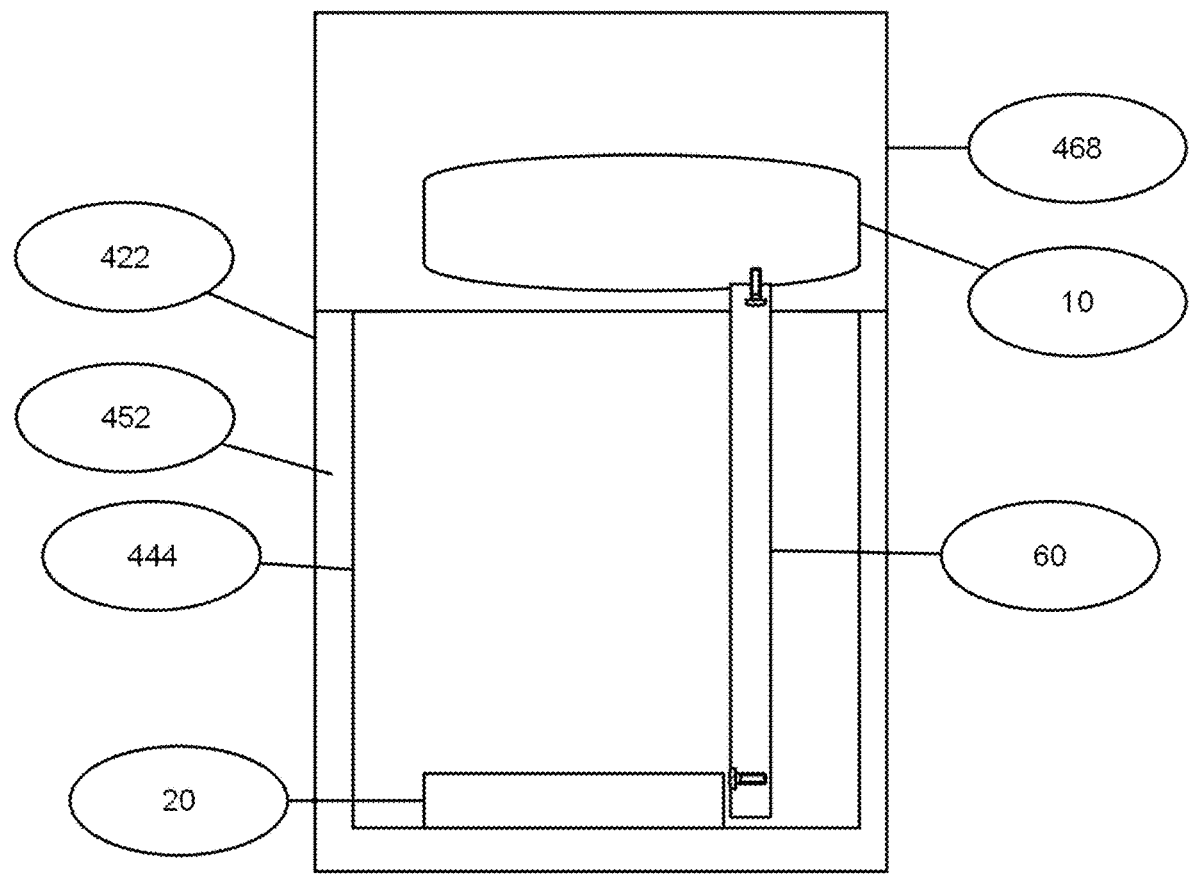
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, minicomputers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications.

Figure 7A:
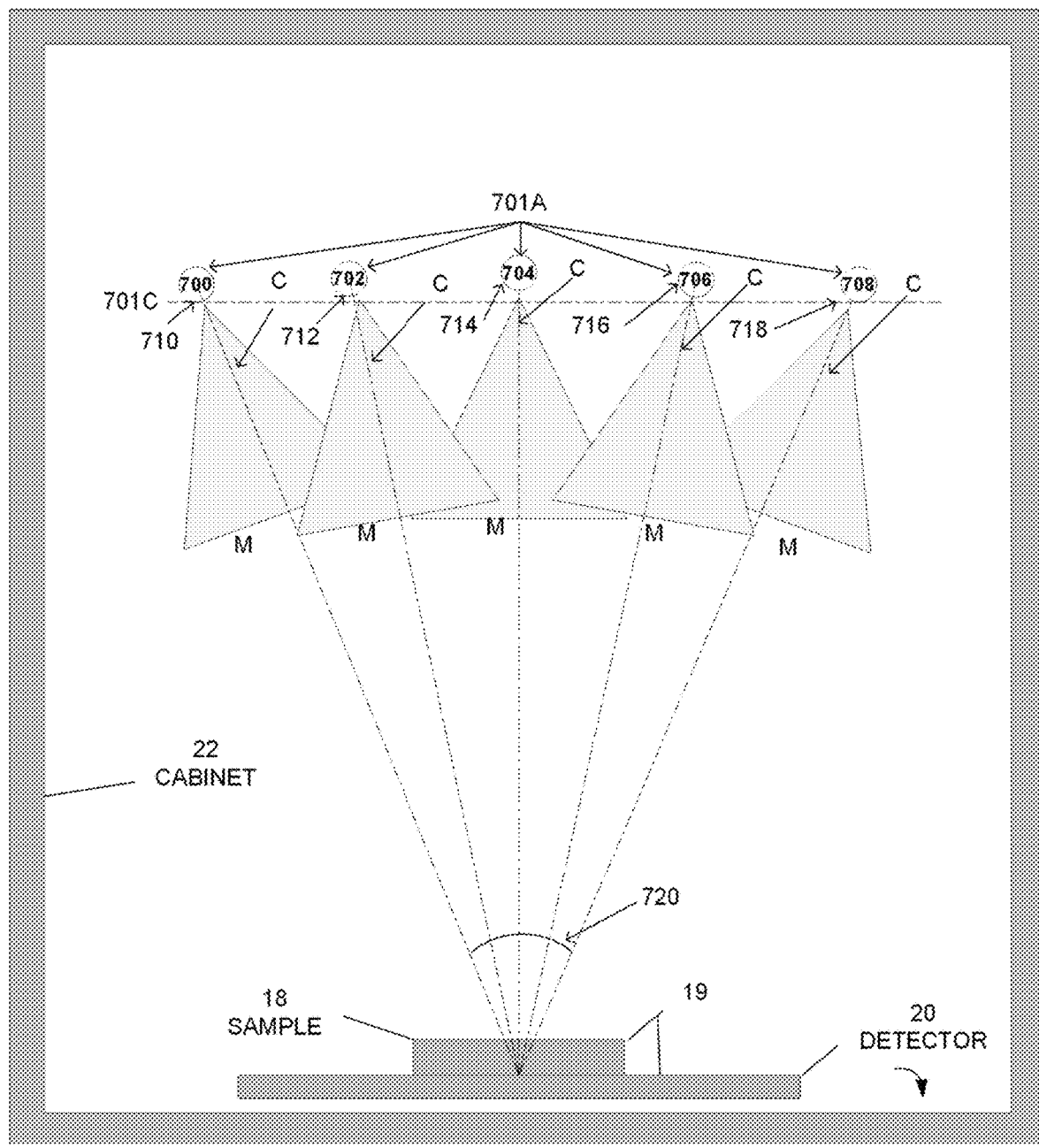
FIGS. 7A—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.
Figure 7B:
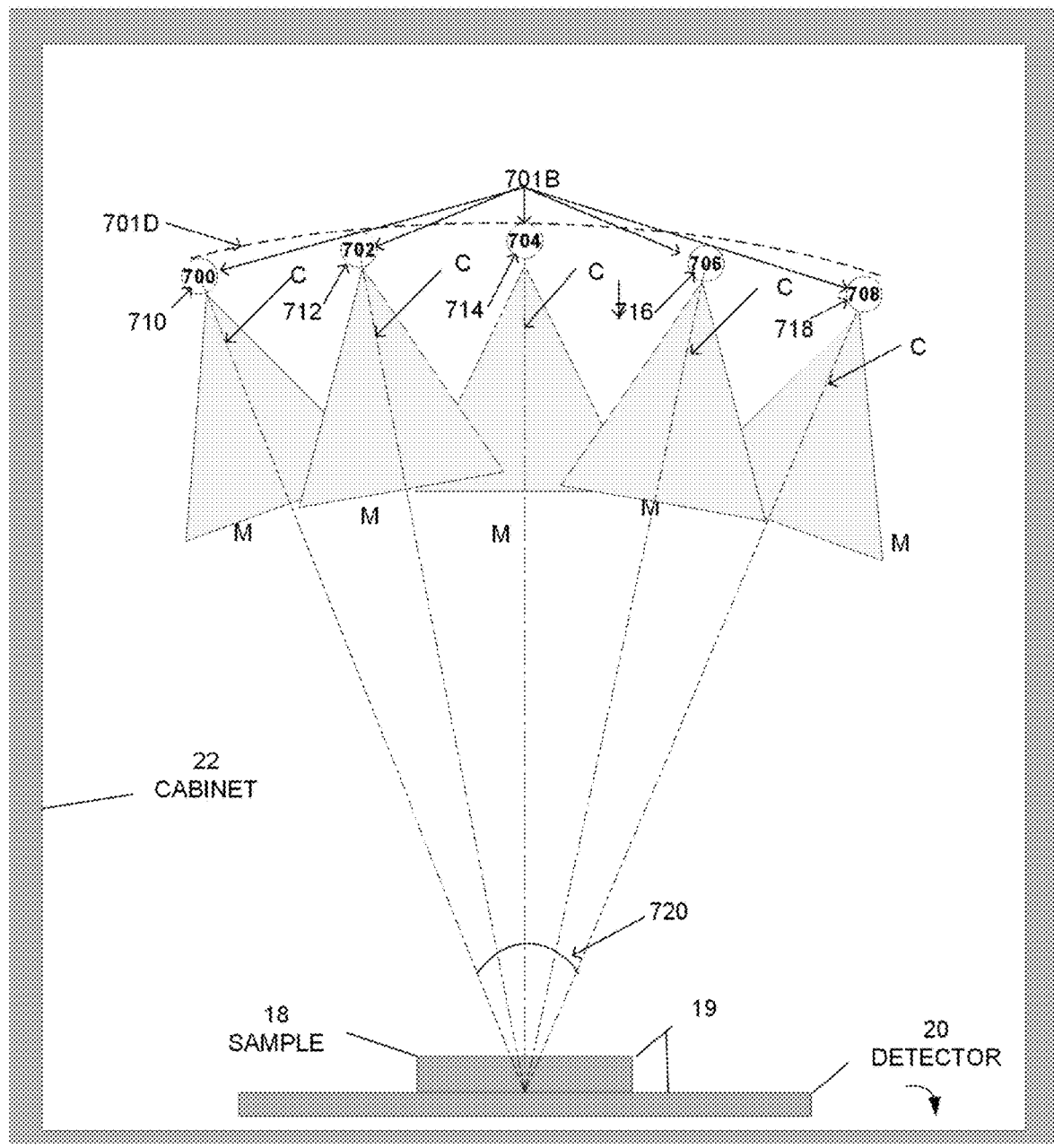
FIGS. 7B—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.

Other embodiment of the present disclosure is illustrated in FIGS. 7A and 7B that operate and include the aspects and features illustrated in the embodiments of FIGS. 1-6 except the embodiments of FIGS. 7A and 7B include an array or plurality of fixed x-ray sources at fixed points, for example, x-ray sources 700, 702, 704, 706 and 708 in place of the travel of x-ray source 10 moving (FIG. 1) swing arm 60 (FIG. 5) servo mechanism. 710, 712, 714, 716 and 718 illustrate exemplary positions of x-ray sources 700, 702, 704, 706 and 708, respectively The aspects of the embodiments illustrated in FIGS. 7A and 7B include at least one array or plurality of x-ray sources 701A positioned in a linear shaped arrangement along substantially linear axis 701C, as shown in FIG. 7A or at least one array or plurality of x-ray sources 701B positioned in an arc shaped arrangement along arc or curved axis 701D, as shown in FIG. 7B. The reference "C" at each of the x-ray sources 700, 702, 704, 706 and 708 in FIGS. 7A and 7B refers to the point source of the X-ray beam from each x-ray source. The reference "M" refers to the spread or fan of the X-ray beam from each x-ray source.

X-ray sources 700, 702, 704, 706 and 708 can be distributed at positions 710, 712, 714, 716 and 718, respectively, in FIGS. 7A and 7B with the end positions of the array, for example, between the point source "C" line of the beam of 700 at position 710 and the point source "C" line of the beam of 708 at position 718, are separated by an arc 720 of from about 20° to about 50°, preferable about 30°, more preferable about 20° with one x-ray source, for example, the point source "C" line of the beam of 704 at position 714 positioned at about 0°. The other x-ray sources 702 at position 712, and 706 at position 716 can be positioned such that each of those x-ray sources are positioned in between x-ray sources 700 and 708 along linear axis 701C, as shown in FIG. 7A or arc or curved axis 701D, as shown in FIG. 7B, preferably evenly spaced. The following are exemplary positions for the embodiments of FIGS. 7 and 7A can be used. Exemplary Configuration 1—about 350° (reference position 710), about 355° (reference position 712), about 0° (reference position 714), about 5° (reference position 716) and about 10° (reference position 718); Exemplary Configuration 2—about 340° (reference position 710), about 350° (reference position 712), about 0° (reference position 714), about 10° (reference position 716) and about 20° (reference position 718); Exemplary Configuration 3—about 335° (reference position 710), about 347.5° (reference position 712), about 0° (reference position 714), about 12.5° (reference position 716) and about 25° (reference position 718); between approximately 340° (reference position 12) to 0° (reference position 14) to 20° (reference position 16) and or between approximately 335° (reference position 12) to 0° (reference position 14) to 25° (reference position 16).

In another embodiment, X-ray sources 700, 702, 704, 706 and 708 can be positioned at 710, 712, 714, 716 and 718, respectively, in FIGS. 7A and 7B, such that the point source "C" line of the beam of each the x-ray sources at either end of the array, the point source "C" line of the beam of 700 at position 710 and the point source "C" line of the beam of 708 at position 718, are separated by an arc 720 of from about 20° to about 50° arc, preferable about 30°, more preferable about 20°, with one x-ray source the point source "C" line of the beam of 704 at position 714 is positioned at about 0°. The other x-ray sources 702 at position 712, and 706 at position 716 can be positioned such that the point source "C" of the beam of each of those x-ray sources are positioned within arc 720, preferable with the point source "C" line of the beams of x-ray sources 702 at position 712, 704 at position 714 and 706 at position 716 are evenly distributed between the point source "C" line of the beam x-ray sources 700 at position 710 and 708 at position 718. For example, x-ray source 700 can be positioned with a point source "C" line of the beam thereof at about 350°, x-ray source 702 can be positioned with a point source "C" line of the beam thereof at about 355°, x-ray source 704 can be positioned with a point source "C" line of the beam thereof at about 0°, x-ray source 706 can be positioned with a point source "C" line of the beam thereof at about 5° and x-ray source 708 can be positioned with a point source "C" line of the beam thereof at about 10°. For another example, x-ray source 700 can be positioned with a point source "C" line of the beam thereof at about 340°, x-ray source 702 can be positioned with a point source "C" line of the beam thereof at about 350°, x-ray source 704 can be positioned with a point source "C" line of the beam thereof at about 0°, x-ray source 706 can be positioned with a point source "C" line of the beam thereof at about 10° and x-ray source 708 can be positioned with a point source "C" line of the beam thereof at about 20°. For still another example, x-ray source 700 can be positioned with a point source "C" line of the beam thereof at about 335°, x-ray source 702 can be positioned with a point source "C" line of the beam thereof at about 347.5°, x-ray source 704 can be positioned with a point source "C" line of the beam thereof at about 0°, x-ray source 706 can be positioned with a point source "C" line of the beam thereof at about 12.5° and x-ray source 708 can be positioned with a point source "C" line of the beam thereof at about 25°.

The ranges recited herein are intended to be approximate and inclusive of start and endpoints.

The number of x-ray sources in the arrays or pluralities of x-ray sources 701A and 701B can range from a minimum total of at least about 3 to about 11 or more, about 5 to about 11 (preferably about 5, about 7, about 9, about 11) including preferably an odd number of x-ray sources, further including for each of these aforementioned ranges wherein one of the x-ray sources is positioned at about 0° or the point source "C" line of one of the x-ray beams is positioned at about 0°. An alternative embodiment can include arrays or pluralities of x-ray sources 701A and 701B distributed such that the point sources of adjacent x-ray sources in the array or plurality are separated by about 1° to about 5°, preferably about 1°. As with other embodiments of the present disclosure the x-ray detector 20 is stationary as is the sample 18 and the x-ray detector can include, for example, a flat panel x-ray detector including a flat panel digital x-ray detector. The x-ray cabinet 22, the detector 20, the sample 18 and the specimen platform 19 (which is a protective cover) or other surface of the detector 20 are the same as included in the embodiment of FIG. 1. As with other embodiments of the present disclosure, the isocenter of the image acquisition geometry is located below the sample, on the surface of the detector.

Each x-ray source of the array or plurality (e.g., x-ray sources 700, 702, 704, 706 and 708) can be activated to emit an x-ray beam one at a time so that the detector 20 receives only one image at a time. The sequence of activating the x-ray sources can be random, but preferably, from left to right (e.g., first 700, second 702, third 704, fourth 706 and fifth 708) or right to left (e.g., first 708, second 706, third 704, fourth 702 and fifth 700).

Operation of the embodiments of FIGS. 7A and 7B that is different from what is included in the present disclosure in FIG. 3 includes at 316 the detector 20 capturing images from x-rays emitted from each of the fixed x-ray sources ((e.g., x-ray sources 700, 702, 704, 706 and 708) that are included in the array or plurality of x-ray sources and storing the captured image along with the identification of the specific x-ray source ((e.g., x-ray sources 700, 702, 704, 706 and 708) from which it originated, using the latter information to identify the position of the x-ray source relative to the sample. The captured images and identification of the specific x-ray source ((e.g., x-ray sources 700, 702, 704, 706 and 708) from which each originated are stored 318 and digital tomosynthesis is performed 320. The tomosynthesis image is then displayed 324.

One advantage of having a fixed array of x-ray sources (compared to, for example, having one x-ray source that is moved by, e.g., a motion control mechanism) is the elimination of moving parts needed to move the single x-ray source, the elimination of vibration caused by x-ray source movement during use which could cause blurring or artifacts, the faster acquisition of x-ray images as energizing each of the plurality of x-ray sources need only rely on computer controlled and don't need to wait until the single x-ray source is moved into position, and a more precise angle resolution because each of the x-ray source in the plurality or array are fixed in position rather than having to rely on a moving x-ray source where its position can be less precise during operation.

Figure 8:
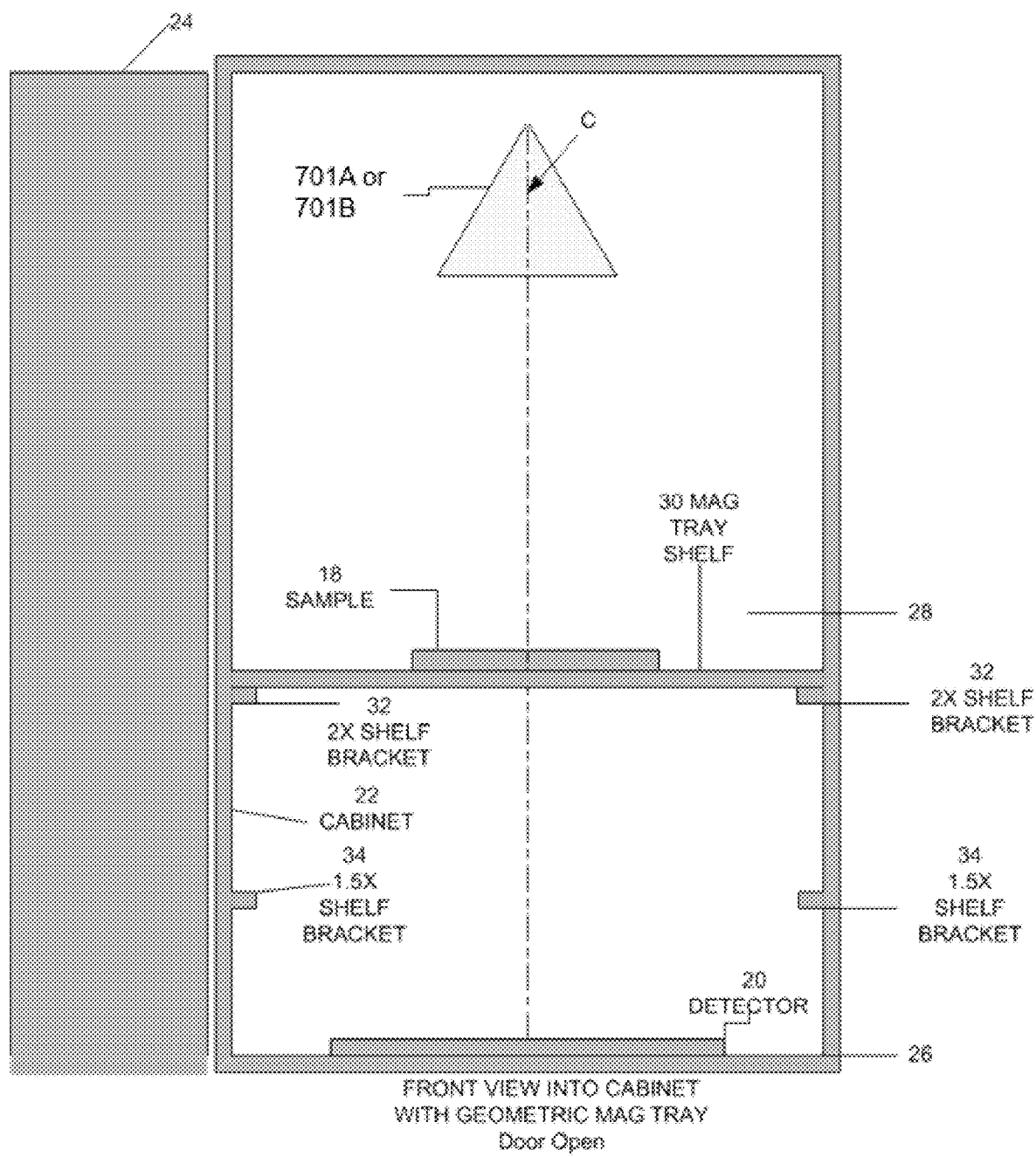
FIG. 8—Displays an exemplary orientation of the embodiments of FIGS. 7A and 7B but with the sample geometrically magnified on a raised sample tray as well as the magnification shelfs brackets in one embodiment of a system incorporating aspects of the present disclosure.

Another embodiment of a system incorporating aspects of the present disclosure is illustrated in FIG. 8. FIG. 8 schematically illustrates the orientation of the mechanism as seen when the door is opened, similar to FIG. 2. The x-ray sources in the array or plurality of x-ray sources 701A and 701B in FIGS. 7A and 7B will generally activate from the back to the front (left to right in FIGS. 7A and 7B) or right to left (right to left in FIGS. 7A and 7B) with the detector 20 orientated at the base of the cabinet chamber 22. The reference "C" refers to the point source of the X-ray beam. The reference "M" refers to the spread or fan of the X-ray. Illustration is provided when the sample is elevated above the detector on the magnification tray 30 to affect geometric magnification. Geometric magnification is achieved by moving the movable magnification tray 30 closer to the x-ray sources (the array or plurality of x-ray sources 701A and 701B in FIGS. 7A and 7B) brackets on which the magnification tray 30 is supported, the brackets being to mounted (permanently or temporarily) to the sides (interior walls) of the cabinet at different distances from the detector 20. In this example, brackets 32 could produce a 2× magnification of sample 18 when magnification tray 30 with sample 18 is positioned on brackets 32 and brackets 34 could produce a 1.5× magnification of sample 18 when magnification tray 30 with sample 18 is positioned on brackets 34. However, these are exemplified magnification powers and shelf bracket heights and are not to be considered limiting. If we affix shelf bracket 32 and the magnification tray 30 closer to the x-ray sources, we will attain a greater geometric magnification—3× or more. The magnification tray 30 is normally kept outside the x-ray chamber 28, for example, when sample 18 is positioned on detector 20, as illustrated, for example, in FIG. 1 and is constructed of a non-metallic, radio translucent (x-ray transparent) material such as plastic or carbon fibre.

Figure 9:
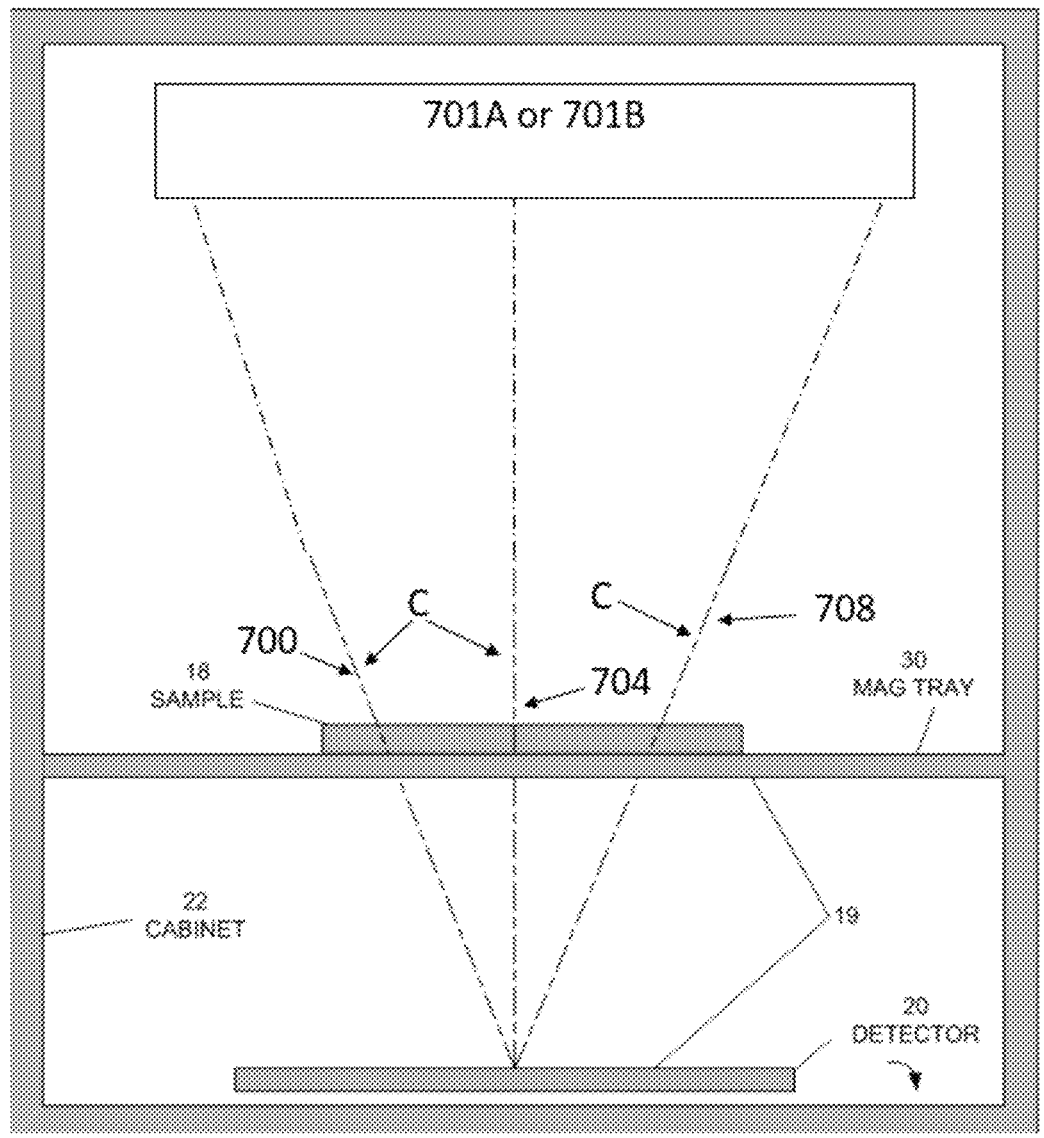
FIG. 9—Displays FIGS. 7A and 7B but with the sample geometrically magnified on a raised sample tray in one embodiment of a system incorporating aspects of the present disclosure.

FIG. 9 schematically displays items as described in FIGS. 7A and 7B but the difference is that the sample is raised above the detector to effect geometric magnification with distance above the detector 19 illustrated. Although only point source "C" lines of the x-ray beams of x-ray sources 700, 704 and 708 are shown, the number of x-ray sources in the embodiments illustrated in FIG. 9 are not limited to 3 and can be as disclosed in the present disclosure.

Figures 10A, 10B, 10C:
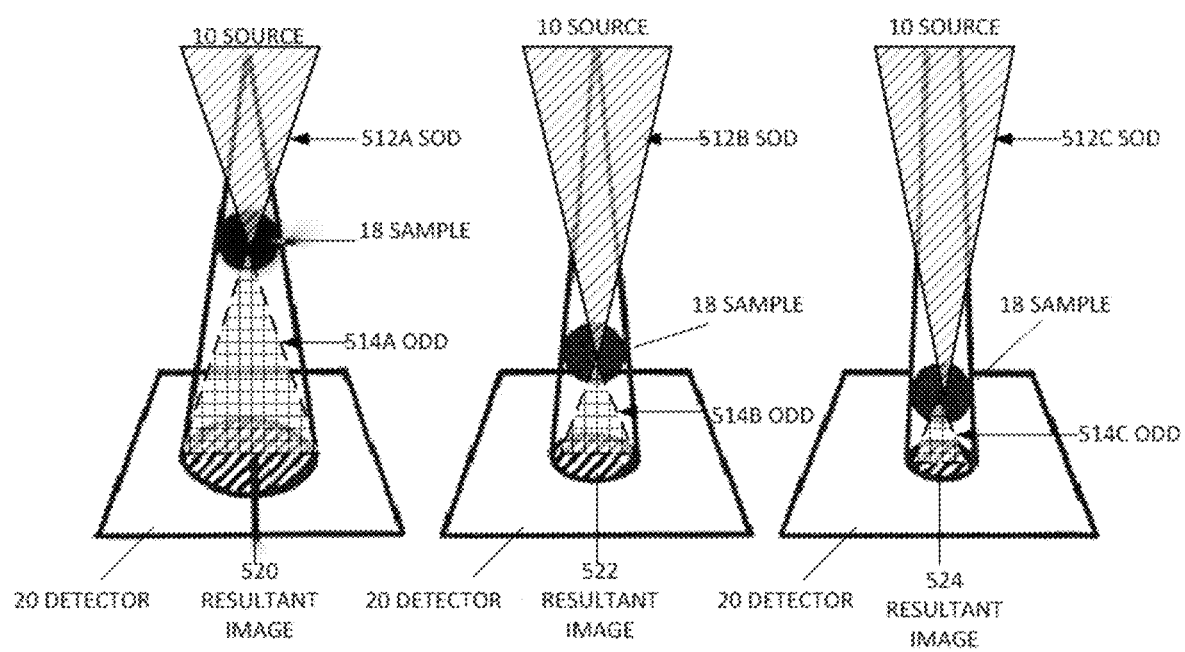
FIGS. 10A, 10B, and 10C—Display examples and theories of x-ray geometric magnification.

FIGS. 10A, 10B and 10C illustrate geometric magnification. Geometric magnification results from the detector being farther away from the X-ray source than the object. In this regard, the source-detector distance or SDD 510 (also called the source to image-receptor distance or SID) is a measurement of the distance between the x-ray tube 10 and the detector 20. The estimated radiographic magnification factor (ERMF) is the ratio of the source-detector distance 510 (SDD) over the source-object distance 512 (SOD). The source-detector distance 510 (SDD) is roughly related to the source-object distance 512 (SOD) and the object-detector distance 514 (ODD) by the equation SOD 512+ODD 514=SDD 510.

Similar to a lens in photography, where the sample 18 is positioned relative to the source 10 and detector 20 changes magnification and field of view. Three terms are used to describe positioning: source-object distance 512 (SOD, where the object represents the sample); object-image distance 514 (O1D, where the image is the detector 20); and source-image distance (SID) or source detector distance 510 (SDD). The effects of moving the sample 18 and detector 20 can be seen by the method of similar triangles. In the example as shown in FIGS. 10A, 10B and 10C as the top triangles 512A, 512B and 512C (cross hatch fill) get shorter going from FIG. 10A to FIG. 10B to FIG. 10C, the bottom triangles 514A, 514B and 514C (checker fill) get longer and the base of the triangles 526A, 526B and 526C gets wider effecting magnification on the detector 20 and the magnification of the resulting images 520, 522 and 524.

In FIG. 10B the sample 18 is moved away from the source 10 and the resultant image 520, 522, 524 goes down in size (less magnified) as the sample 18 moves closer to the detector 20. Differences in magnification are exhibited by the differing triangle lengths and the resultant image which represent the source-object distance 512 (SOD) and the object-detector distance 514 (ODD). Preferably for geometric magnification, the sample 18 is supported by a magnification tray 30 (in FIGS. 8 and 9) to be imaged.

Embodiments of the present disclosure include a cabinet x-ray system for of obtaining geometric magnifying specimen x-ray images, projection x-ray images, and reconstructed tomosynthetic x-ray images of the specimen, the system comprising: a moveable cabinet defining a walled enclosure surrounding an interior chamber and a door configured to cover the interior chamber; an x-ray source, a flat panel digital x-ray detector, a specimen platform including a magnification tray that is positioned at a distance above the flat panel digital x-ray detector to facilitate geometric magnification imaging of the specimen in the cabinet and a motion control mechanism configured for moving the x-ray source to or along a plurality of positions within the interior chamber relative to the specimen disposed on the specimen platform; and a controller configured to: selectively energize the x-ray source to emit x-rays through the specimen to the flat panel digital x-ray detector at selected positions of the x-ray source relative to the specimen such that the isocenter of the emitted x-rays at the selected positions is located at the flat panel digital x-ray detector surface, wherein the controller is configured to: control the flat panel digital x-ray detector to collect projection x-ray images of the specimen when the x-ray source is energized at the selected positions, wherein one of the projection x-ray images is a two-dimensional x-ray image taken at standard imaging angle of about 0°; create a tomosynthetic x-ray image reconstructed from a collection of projection x-ray images; process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image and the one or more reconstructed tomosynthetic x-ray images.

Embodiment of the present disclosure include a cabinet x-ray system wherein the specimen platform is capable of being positioned within the chamber at a plurality of distances above the flat panel digital x-ray detector to facilitate geometric magnification imaging of the specimen.

The embodiments of the present disclosure may include an x-ray source that is a micro-focus X-ray source.

Embodiments of the present disclosure also include a computing device comprising: at least with one controller processor, and at least on module (x-ray source, detector, etc.) operable by the at least one controller processor to: output, for display; determining, based on the video data, a display action; and responsive to determining the preference/initiated action, output for display the resultant images attained by the x-ray cabinet system.

Embodiments of the present disclosure also include stationary x-ray cabinet digital tomosynthesis system comprising: a field emission x-ray source that generates x-ray radiation from an array of spatially distributed x-ray focal spots configured to image a specimen contained in a cabinet from different viewing angles by electronically activating a corresponding array of spatially distributed field emission cathodes; an area x-ray detector configured to detect the projection images of the specimen; an electronic controller for activating the x-ray radiation from the different x-ray focal spots in the x-ray source in a sequence and for synchronizing x-ray exposure from a given focal spot with image collection by the x-ray detector; and wherein tomography images of the specimen are reconstructed using a plurality of projection images of the specimen collected from different viewing angles without moving any of the x-ray source, the specimen, or the x-ray detector.

The embodiments of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cabinet x-ray system for obtaining specimen x-ray images, projection x-ray images, and reconstructed tomosynthetic x-ray images of a specimen, the cabinet x-ray system comprising:
   a cabinet defining an interior chamber;
   a display;
   an x-ray system including:
      an x-ray detector;
      a plurality of fixed x-ray sources in an array, the plurality of fixed x-ray sources including fixed x-ray sources at end positions of the array, each fixed x-ray source of the fixed x-ray sources at the end positions of the array having a point source line of a beam such that an angle between point source lines of the fixed x-ray sources at the end positions of the array is from about 20° to about 50°, about 30°, or about 20°, wherein one of the plurality of fixed x-ray sources is positioned at a standard imaging angle of approximately 0° relative to the x-ray detector; and
      a specimen platform; and
   a controller configured to:
      energize each of the plurality of fixed x-ray sources separately to emit x-rays through the specimen to the x-ray detector such that an isocenter of the emitted x-rays of each of the plurality of fixed x-ray sources is located at a surface of the x-ray detector;
      control the x-ray detector to collect projection x-ray images of the specimen when each of the plurality of fixed x-ray sources are separately energized to form a collection of x-ray images, wherein one of the projection x-ray images is a two-dimensional x-ray image taken at the standard imaging angle of approximately 0°;
      create a tomosynthetic x-ray image reconstructed from the collection of projection x-ray images;
      process the collection of the projection x-ray images in the controller into one or more reconstructed tomosynthetic x-ray images representing a volume of the specimen and relating to one or more image planes that are selectively same or different from that of the two-dimensional x-ray image; and
      selectively display the two-dimensional x-ray image and the one or more reconstructed tomosynthetic x-ray images.

2. The cabinet x-ray system of claim 1, wherein the cabinet comprises a walled enclosure surrounding the interior chamber, a door configured to cover the interior chamber, and a sampling chamber within the interior chamber for containing the specimen.

3. The cabinet x-ray system of claim 1, wherein the specimen platform is configured for excised tissue, organ, or bone specimens.

4. The cabinet x-ray system of claim 1, wherein the specimen platform is configured for any organic or inorganic specimen that fits inside the cabinet.

5. The cabinet x-ray system of claim 1, wherein the specimen platform having a protective cover of and in physical contact with the x-ray detector.

6. The cabinet x-ray system of claim 1, wherein the plurality of fixed x-ray sources includes at least three x-ray sources.

7. The cabinet x-ray system of claim 1, wherein the plurality of fixed x-ray sources includes at least five x-ray sources.

8. The cabinet x-ray system of claim 1, wherein the plurality of x-ray sources are positioned in a linear or arc-shaped arrangement.

9. A cabinet x-ray system for obtaining specimen x-ray images, projection x-ray images, and reconstructed tomosynthetic x-ray images of a specimen, the cabinet x-ray system comprising:
   a cabinet defining an interior chamber;
   a display;
   an x-ray system including:
      a flat panel x-ray detector;
      a plurality of x-ray sources, wherein one of the plurality of x-ray sources is positioned at a standard imaging angle of approximately 0° relative to the flat panel x-ray detector; and
      a specimen platform including a magnification tray that is positioned at a distance above the flat panel x-ray detector to facilitate geometric magnification imaging of the specimen in the cabinet; and
   a controller configured to:
      energize each of the plurality of x-ray sources separately to emit x-rays through the specimen to the flat panel x-ray detector such that an isocenter of the emitted x-rays of each of the plurality of x-ray sources is located at a surface of the flat panel x-ray detector;
      control the flat panel x-ray detector to collect projection x-ray images of the specimen when each of the plurality of x-ray sources are separately energized to form a collection of x-ray images, wherein one of the projection x-ray images is a two-dimensional x-ray image taken at the standard imaging angle of approximately 0°;
      create a tomosynthetic x-ray image reconstructed from the collection of projection x-ray images;
      process the collection of the projection x-ray images in the controller into one or more reconstructed tomosynthetic x-ray images representing a volume of the specimen and relating to one or more image planes that are selectively same or different from that of the two-dimensional x-ray image; and
      selectively display the two-dimensional x-ray image and the one or more reconstructed tomosynthetic x-ray images.

10. The cabinet x-ray system of claim 9, wherein the cabinet comprises a walled enclosure surrounding the interior chamber, a door configured to cover the interior chamber, and a sampling chamber within the interior chamber for containing the specimen.

11. The cabinet x-ray system of claim 9, wherein the specimen platform is configured for excised tissue, organ, or bone specimens.

12. The cabinet x-ray system of claim 9, wherein the specimen platform is configured for any organic or inorganic specimen that fits inside the cabinet.

13. The cabinet x-ray system of claim 9, wherein the plurality of x-ray sources includes at least three x-ray sources.

14. The cabinet x-ray system of claim 9, wherein the plurality of x-ray sources includes at least five x-ray sources.

15. The cabinet x-ray system of claim 9, wherein the plurality of x-ray sources are positioned in a linear or arc-shaped arrangement in a range of from about 350° to about 10°, or front about 340° to about 20°, or a maximum of about 355° to 25°.

16. A method for obtaining and varying a superimposed image of an x-ray image and an optical image of a specimen in a cabinet x-ray and optical image system, wherein the cabinet x-ray and optical image system comprises:
   a cabinet defining an interior chamber;
   a display;
   an x-ray system including:
      an x-ray detector;
      a plurality of fixed x-ray sources in an array, the plurality of fixed x-ray sources including fixed x-ray sources at end positions of the array, each fixed x-ray source of the fixed x-ray sources at the end positions of the array having a point source line of a beam such that an angle between point source lines of the fixed x-ray sources at the end positions of the array is from about 20° to about 50°, about 30°, or about 20°, wherein one of the plurality of fixed x-ray sources is positioned at a standard imaging angle of approximately 0° relative to the x-ray detector; and
      a specimen platform; and
   a controller configured to:
      energize each of the plurality of fixed x-ray sources separately to emit x-rays through the specimen to the x-ray detector such that an isocenter of the emitted x-rays of each of the plurality of fixed x-ray sources is located at a surface of the x-ray detector;
      control the x-ray detector to collect projection x-ray images of the specimen when each of the plurality of fixed x-ray sources are separately energized to form a collection of x-ray images, wherein one of the projection x-ray images is a two-dimensional x-ray image taken at the standard imaging angle of approximately 0°;
      create a tomosynthetic x-ray image reconstructed from the collection of projection x-ray images;
      process the collection of the projection x-ray images in the controller into one or more reconstructed tomosynthetic x-ray images representing a volume of the specimen and relating to one or more image planes that are selectively same or different from that of the two-dimensional x-ray image; and
      selectively display the two-dimensional x-ray image and the one or more reconstructed tomosynthetic x-ray images,
   wherein the method comprises:
      controlling the x-ray detector to collect projection x-ray images of the specimen when each of the plurality of x-ray sources are separately energized to form a collection of x-ray images, wherein one of the projection x-ray images is a two-dimensional x-ray image taken at a standard imaging angle of approximately 0°;
      creating a tomosynthetic x-ray image reconstructed from the collection of projection x-ray images;
      processing the collection of the projection x-ray images in the controller into one or more reconstructed tomosynthetic x-ray images representing a volume of the specimen and relating to one or more image planes that are selectively same or different from that of the two-dimensional x-ray image; and
      selectively displaying the two-dimensional x-ray image and the one or more reconstructed tomosynthetic x-ray images.

17. The method of claim 16, wherein the cabinet comprises a walled enclosure surrounding the interior chamber, a door configured to cover the interior chamber, and a sampling chamber within the interior chamber for containing the specimen.

18. The method of claim 16, wherein the specimen platform is configured for excised tissue, organ, or bone specimens.

19. The method of claim 16, wherein the specimen platform is configured for any organic or inorganic specimen that fits inside the cabinet.

20. The method of claim 16, further comprising the specimen platform having a protective cover of and in physical contact with the x-ray detector.

* * * * *